(12) United States Patent
Nguyen et al.

(10) Patent No.: US 6,918,917 B1
(45) Date of Patent: *Jul. 19, 2005

(54) MINIMALLY INVASIVE ANNULOPLASTY PROCEDURE AND APPARATUS

(75) Inventors: John D. Nguyen, San Jose, CA (US); Arthur Hill, San Francisco, CA (US); Laurent Schaller, Los Altos, CA (US)

(73) Assignee: Medtronic, Inc., Minneapolis, MN (US)

( * ) Notice: Subject to any disclaimer, the term of this patent is extended or adjusted under 35 U.S.C. 154(b) by 261 days.

This patent is subject to a terminal disclaimer.

(21) Appl. No.: 09/686,729

(22) Filed: Oct. 10, 2000

(51) Int. Cl.$^7$ .............................................. A61B 17/10
(52) U.S. Cl. ..................................... 606/139; 623/2.38
(58) Field of Search ................................ 606/139, 151, 606/153, 157, 158, 191, 192, 193, 194, 195, 219, 222, 223, 76, 78, 140–143, 174; 604/95.05; 24/81, 115, 225; 623/2.4, 2.41, 2.38, 2.39, 2.42; D24/145

(56) References Cited

U.S. PATENT DOCUMENTS

| | | | |
|---|---|---|---|
| 3,656,185 A | | 4/1972 | Carpentier |
| 3,825,009 A | | 7/1974 | Williams |
| 4,042,979 A | | 8/1977 | Angell |
| 4,185,636 A | * | 1/1980 | Gabbay et al. ......... 128/334 R |
| 4,396,139 A | | 8/1983 | Hall et al. |
| 4,492,229 A | * | 1/1985 | Grunwald ............... 128/303 R |

(Continued)

FOREIGN PATENT DOCUMENTS

| | | |
|---|---|---|
| WO | WO 99/62406 A2 | 12/1999 |
| WO | WO 99/62409 A1 | 12/1999 |
| WO | WO 00/03759 A2 | 1/2000 |
| WO | WO00/60995 | * 10/2000 |
| WO | WO 00/64381 A2 | 11/2000 |
| WO | WO 00/74603 A1 | 12/2000 |
| WO | WO 01/26586 A1 | 4/2001 |
| WO | WO 03/053289 A1 | 7/2003 |

OTHER PUBLICATIONS

Chitwood Jr., W. Randolph. Mitral Valve Repair: Ischemic (Mastery of Cardiothoracic Surgery, Lippencott–Raven Publishers (1998) 309–321).

Yun, Kwok L., and Miller, Craig D. Mitral Valve Replacement (Mastery of Cardiothoracic Surgery (Lippincott–Raven Publishers (1998) 329–341).

(Continued)

*Primary Examiner*—Alissa L. Hoey
(74) *Attorney, Agent, or Firm*—Tom Berry; Jeffrey J. Hohenshell

(57) ABSTRACT

Clips of a self-closing type are used in annuloplasty procedures. Each clip is generally U-shaped with two end points separated from each other when it is constrained to be in an open configuration, but tends to coil up to assume its naturally closed configuration if the constraint is removed. A plurality of such clips in open configurations penetrate the tissue around the annulus circumferentially and then the constraint keeping them in the open configuration is removed such that they pull the tissue together between their two end points and this tends to reduce the diameter of the annulus. Such clips may be deployed each in the form of a clip assembly, having at least one of its end points connected to a needle through a flexible member and a release mechanism by which the clip can be easily released. The needle is caused to penetrate the tissue at one position and to come out therefrom at another circumferentially separated positions. Alternatively, a clip delivery device may be used with a plurality of such clips loaded to a clip-holder serving to keep them in open configurations. A pusher pushes the loaded clips out of the device one at a time. Self-closing clips can be used efficiently also in ring annuloplasty and valve replacement procedures.

3 Claims, 7 Drawing Sheets

U.S. PATENT DOCUMENTS

| | | | |
|---|---|---|---|
| 4,665,917 A | | 5/1987 | Clanton et al. |
| 4,719,917 A | | 1/1988 | Barrows et al. |
| 5,002,563 A | | 3/1991 | Pyka et al. |
| 5,042,707 A | * | 8/1991 | Taheri ..................... 606/123 |
| 5,064,431 A | * | 11/1991 | Gilbertson et al. ............ 623/2 |
| 5,201,880 A | | 4/1993 | Wright et al. |
| 5,304,204 A | | 4/1994 | Bregen |
| 5,306,296 A | * | 4/1994 | Wright et al. .............. 623/2.37 |
| 5,366,479 A | | 11/1994 | McGarry et al. |
| 5,450,860 A | * | 9/1995 | O'Connor ................... 128/898 |
| 5,545,214 A | | 8/1996 | Stevens |
| 5,571,175 A | * | 11/1996 | Vanney et al. ............. 623/2.41 |
| 5,586,983 A | | 12/1996 | Sanders et al. |
| 5,593,424 A | | 1/1997 | Northrup, III |
| 5,715,987 A | | 2/1998 | Kelley et al. |
| 5,720,755 A | | 2/1998 | Dakov |
| 5,779,718 A | | 7/1998 | Green et al. |
| 5,782,397 A | | 7/1998 | Koukline |
| 5,879,371 A | * | 3/1999 | Gardiner et al. ............ 606/224 |
| 5,908,428 A | | 6/1999 | Scirica et al. |
| 5,911,352 A | | 6/1999 | Racenet et al. |
| 5,941,442 A | | 8/1999 | Geiste et al. |
| 5,961,539 A | | 10/1999 | Northrup, III et al. |
| 5,972,024 A | | 10/1999 | Northrup, III et al. |
| 5,976,159 A | | 11/1999 | Bolduc et al. |
| 5,984,959 A | | 11/1999 | Robertson et al. |
| 5,989,268 A | | 11/1999 | Pugsley, Jr. et al. |
| 6,001,110 A | * | 12/1999 | Adams ....................... 606/151 |
| 6,010,531 A | | 1/2000 | Donlon et al. |
| 6,032,849 A | | 3/2000 | Mastri et al. |
| 6,056,751 A | | 5/2000 | Fenton, Jr. |
| 6,074,401 A | | 6/2000 | Gardiner et al. |
| 6,074,418 A | | 6/2000 | Buchanan et al. |
| 6,113,611 A | | 9/2000 | Allen et al. |
| 6,149,658 A | * | 11/2000 | Gardiner et al. ............ 606/139 |
| 6,165,183 A | * | 12/2000 | Kuchn et al. .............. 606/139 |
| 6,179,840 B1 | | 1/2001 | Bowman |
| 6,217,611 B1 | * | 4/2001 | Klostermeyer ............. 623/2.38 |
| 6,250,308 B1 | | 6/2001 | Cox |
| 6,254,615 B1 | * | 7/2001 | Bolduc et al. ............... 606/142 |
| 6,269,819 B1 | | 8/2001 | Oz et al. |
| 6,283,979 B1 | * | 9/2001 | Mers Kelly et al. ......... 606/139 |
| 6,346,112 B2 | * | 2/2002 | Adams ....................... 606/157 |
| 6,368,348 B1 | * | 4/2002 | Gabbay ..................... 623/2.36 |
| 6,514,265 B2 | * | 2/2003 | Ho et al. .................... 606/157 |
| 6,551,332 B1 | * | 4/2003 | Nguyen et al. ............. 606/151 |
| 6,607,541 B1 | * | 8/2003 | Gardiner et al. ............ 606/151 |
| 6,613,059 B2 | * | 9/2003 | Schaller et al. ............. 606/157 |
| 6,641,593 B1 | * | 11/2003 | Schaller et al. ............. 606/157 |

OTHER PUBLICATIONS

Maisano et al., Francesco. The Double–Orifice Technique as a Standardized Approach to Treat Mitral Regurgitation due to Severe Myxomatous Disease: Surgical Technique (European Journal of Cardiothoracic Surgery, vol. 17 (2000) 201–205).

International Search Report PCT/US01/42653, Mar. 14, 2002.

Milo; Derwent Abstract: Publication No. WO 2003053289 A1 Jul. 3, 2003.

Grondin, Pierre, et al.; Carpenter's Annulusd and De Vega's Annuloplasty; Nov. 1975, pp. 852–861. The Journal of Thoracic and Cardiovascular Surgery vol. 70, No. 5, 1975.

Rabago, M.D., Gregorio, et al.; The New De Vega Technique in Tricuspid Annuloplasty; pp. 231–238, J. Cardiovas. Surg., 21, 1980.

Rivera, M.D., R. et al.; Carpentier's Flexible Ring Versus De Vega's Annuloplasty; Feb. 1985, pp. 196–203. J. Thorac. Cardiovasc. Surg. vol. 89, No. 2, 1985.

Holper, K., et al.; Surgery For Tricuspid Insufficiency: Long Term Follow–Up After De Vega Annuloplasty. Thorac. Cardiovasc. Surgeon 41, 1993, pp. 1–8.

Wei, M.D., Jeng, et al; De Vega's Semicircular Annuloplasty For Tricuspid Valve Regurgitation. Ann. Thorac. Surg. 55 1993, pp. 482–285

* cited by examiner

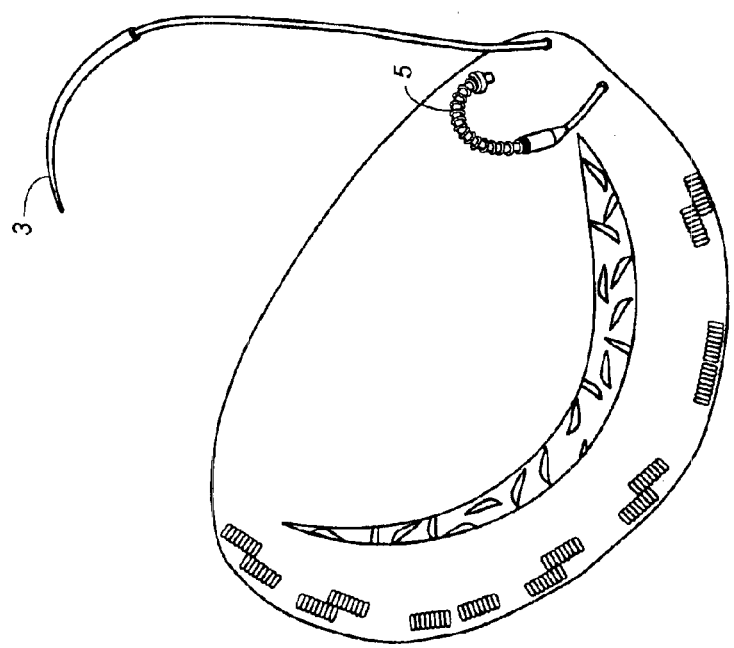
FIG._1
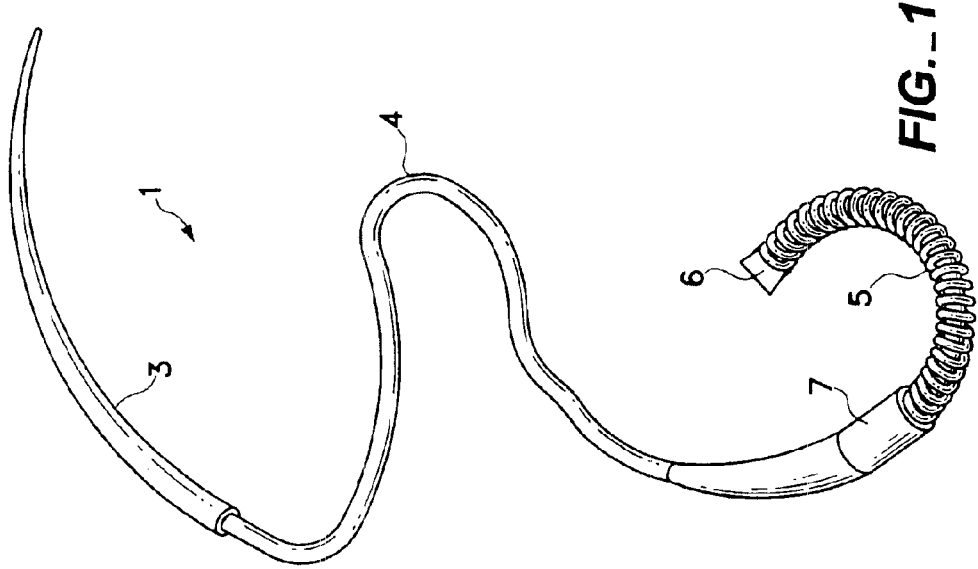
FIG._2

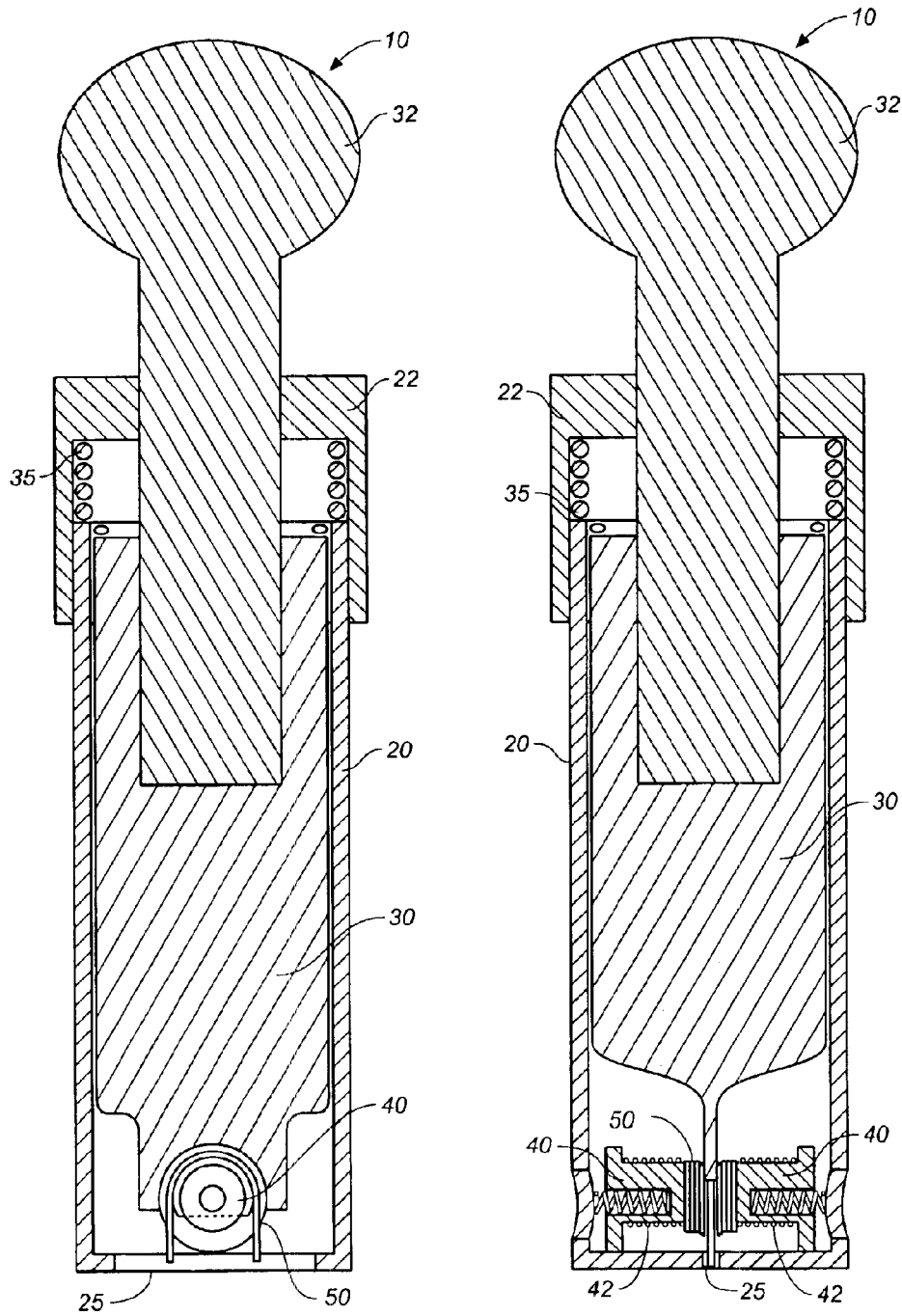

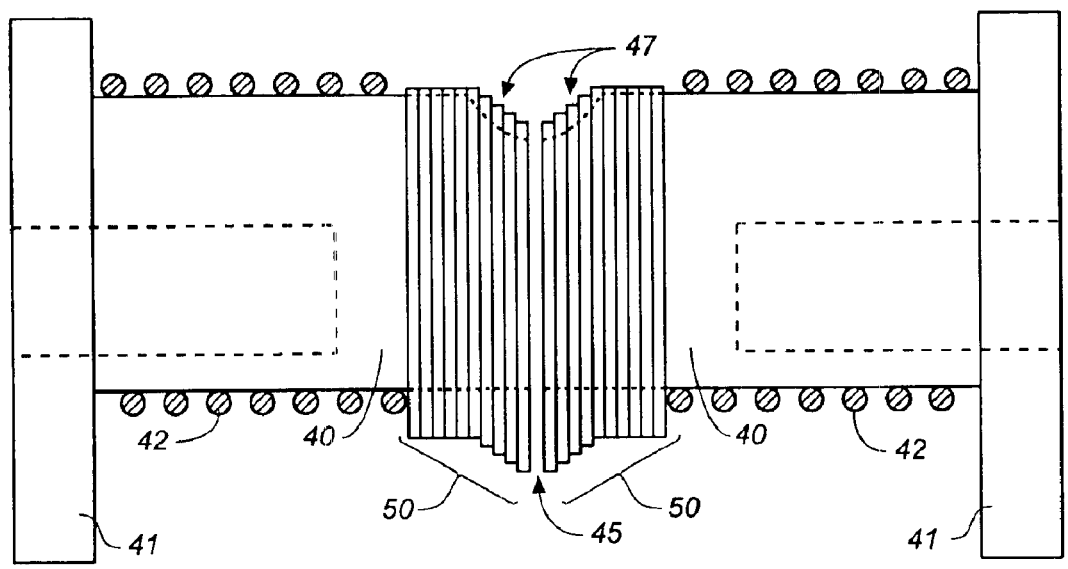
FIG._5
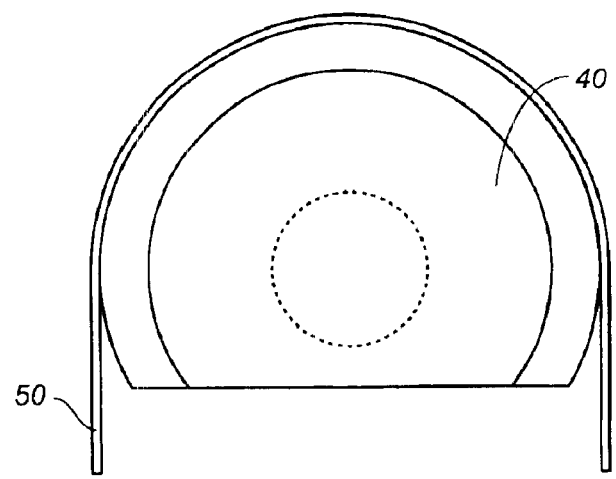
FIG._6

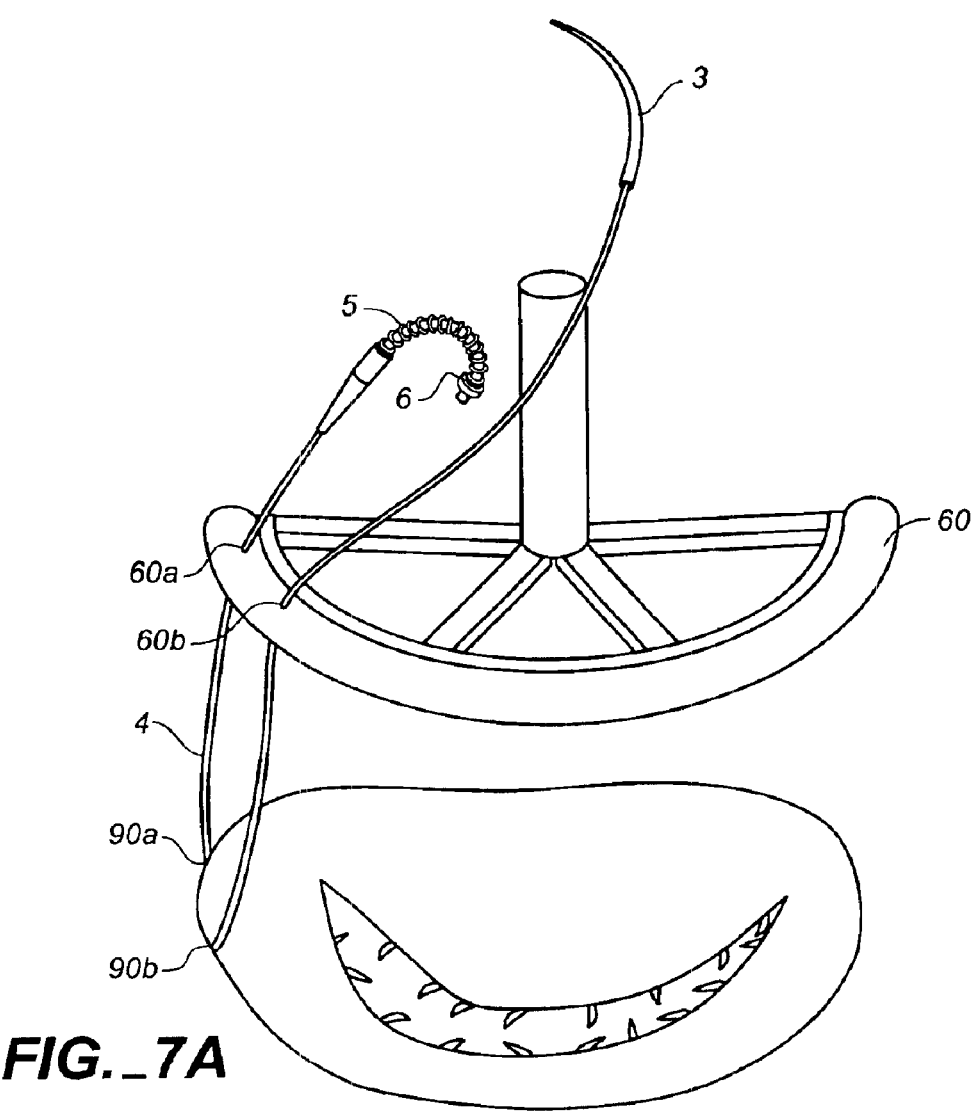
FIG._7A
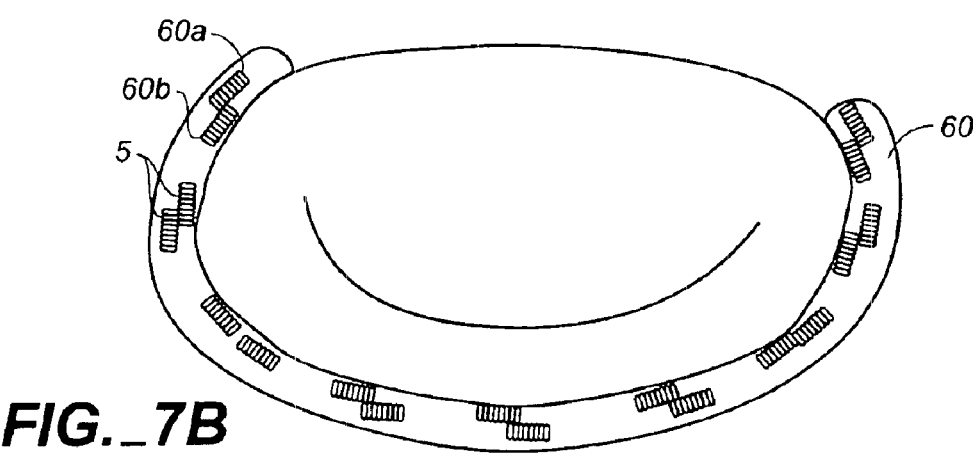
FIG._7B

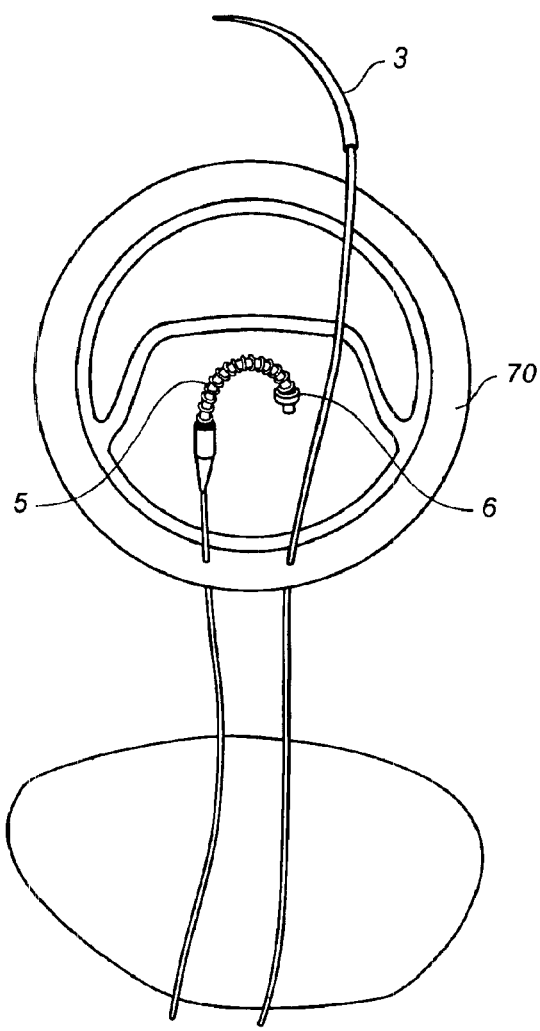
FIG._8A
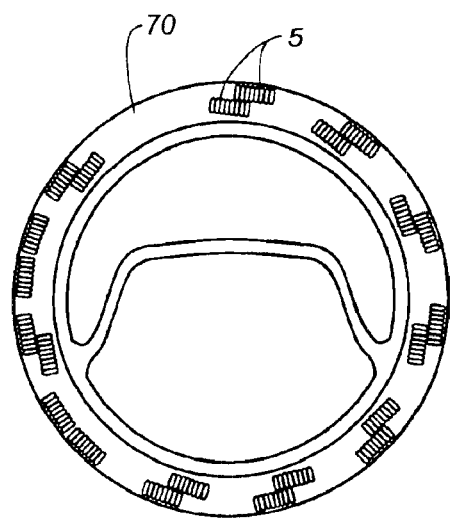
FIG._8B

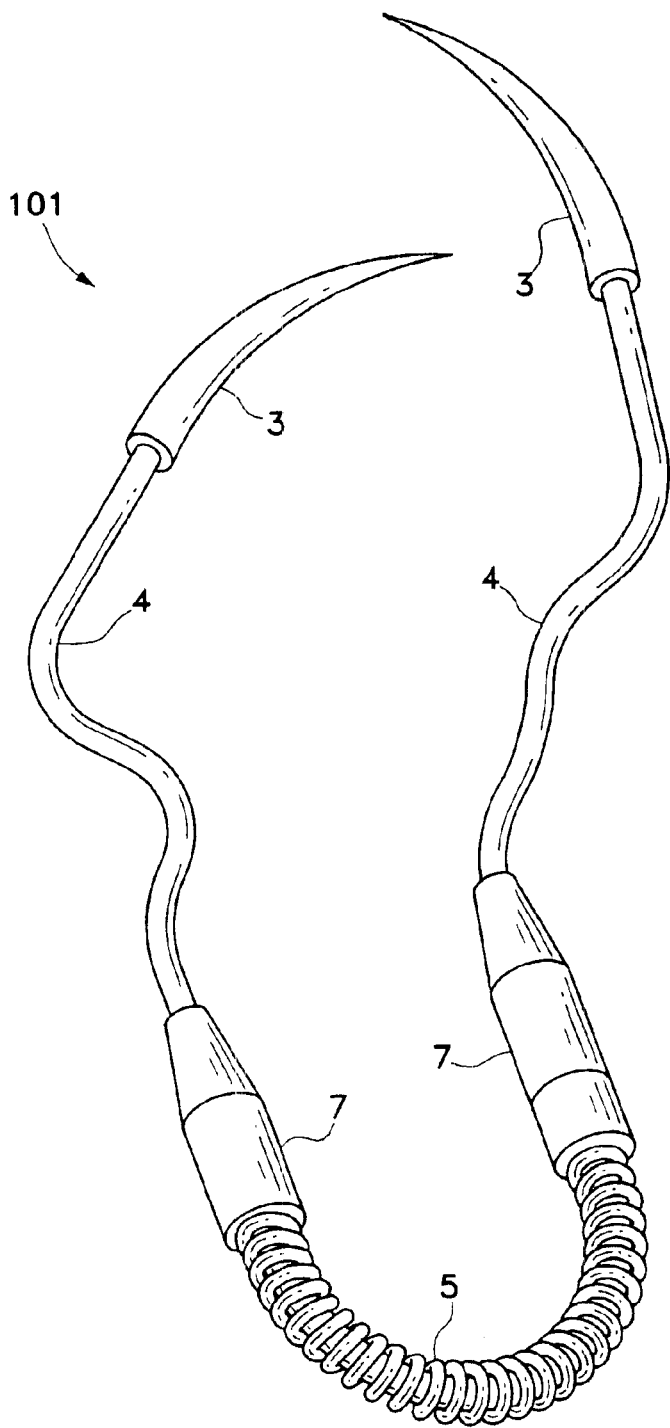
FIG._9

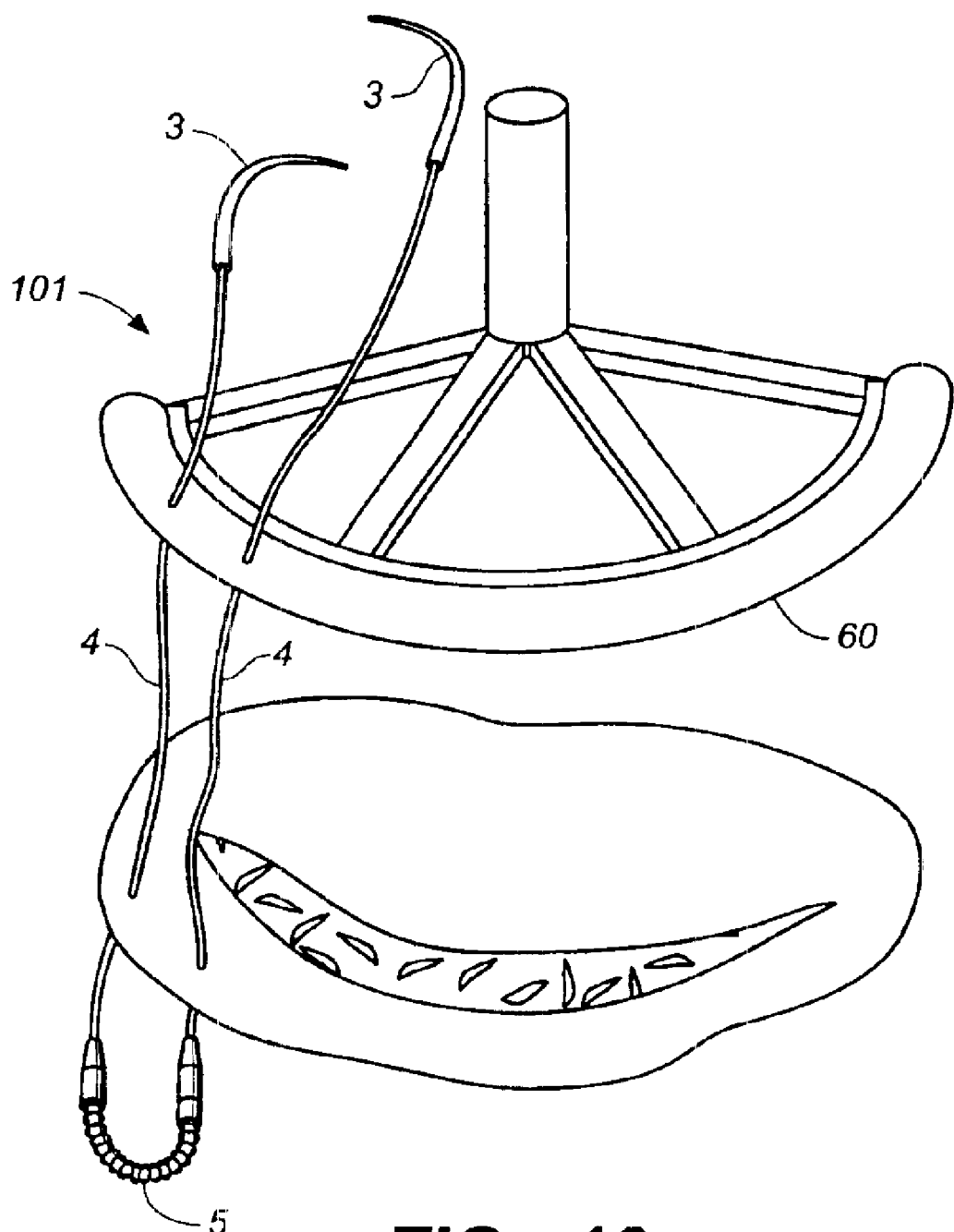
FIG._10

MINIMALLY INVASIVE ANNULOPLASTY PROCEDURE AND APPARATUS

BACKGROUND OF THE INVENTION

This invention relates to methods and apparatus for annuloplasty repair and replacement.

Valve repair and valve replacement are currently done in surgical procedures as described, for example, in "Mitral Valve Repair: Ischemic" by W. Randolph Chitwood, Jr. (Mastery of Cardiothorcic Surgery, Lippincott-Raven Publishers (1998) 309–321) and "Mitral Valve Replacement" by Kwok L. Yun and D. Craig Miller (ibid. (1998) 329–341). Cumbersome suture management, knot tying, pain and long recovery time are inherent to such surgical procedures. It now goes without saying that quickly operable methods and apparatus are desirable for allowing surgeons to perform procedures with less pain and disability than prior art surgical procedures. Tissue-connector apparatus and methods easily usable in such surgical procedures have recently been disclosed in U.S. patent applications Ser. Nos. 09/089,884 and 09/090,305 both filed Jun. 3, 1998 and Ser. Nos. 09/259,705 and 09/260,623 both filed Mar. 1, 2000.

It is therefore an object of this invention to provide simply operable annuloplasty methods and apparatus for valve repair and replacement, not involving cumbersome suture management and suture knotting.

It is another object of this invention to provide such methods and apparatus using the tissue-connector apparatus disclosed in the aforementioned U.S. patent applications filed recently.

SUMMARY OF THE INVENTION

Methods and apparatus embodying this invention with which the above and other objects can be accomplished are characterized as causing clips of a self-closing type to penetrate the tissue around the annulus. Such a clip is typically U-shaped, having two end points, when it is constrained to be in an open configuration but is made of a wire of a shape memory material such that it tends to coil up to assume its naturally closed configuration. Thus, if a plurality of such clips in open configurations penetrate the tissue around the annulus circumferentially and then the constraint keeping them in the open configuration is removed, they pull the tissue together between their two end points, and this tends to reduce the diameter of the annulus.

Such clips may be deployed each in the form of a clip assembly, having one of its end points connected to a tissue-piecing needle through a flexible member such as a suture and a release mechanism by which the clip can be easily released. The clip is then caused to penetrate the tissue at two circumferentially separated positions one after the other. Alternatively, a clip delivery device may be used with a plurality of clips loaded to a clip-holder serving to keep these clips in their open configurations. A pusher is provided for pushing a specified number of such clips out of the device at a time. Clip assemblies of this invention can be effectively used in ring annuloplasty and valve replacement procedures by placing clips circumferentially around a ring or a mitral prosthesis sewing cuff. Cumbersome problems associated with suture management and suture knotting can be thereby obviated.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is an external view of a single-arm clip assembly which may be used in an annuloplasty method embodying this invention;

FIG. 2 is a schematic view of the clip assembly of FIG. 1 being used in an annuloplasty procedure;

FIG. 3 is a sectional front view of a clip delivery device embodying this invention;

FIG. 4 is a sectional side view of the clip delivery device of FIG. 3;

FIG. 5 is a side view of the cartridges shown in FIGS. 3 and 4;

FIG. 6 is an axial view of the cartridge shown in FIGS. 3, 4 and 5;

FIG. 7A is a sketch of the clip assembly of FIG. 1 being used in a ring annuloplasty procedure and FIG. 7B is a sketch of the ring which has been attached to an annulus by a procedure embodying this invention;

FIG. 8A is a sketch of the clip assembly of FIG. 1 being used in a valve replacement procedure and FIG. 8B is a sketch of the mitral prosthesis sewing cuff which has been inserted in a procedure embodying this invention.

FIG. 9 is an external view of a double-arm clip assembly which may be used in an annuloplasty method embodying this invention; and FIG. 10 is a sketch of the clip assembly of FIG. 9 being used in a ring annuloplasty procedure.

Throughout herein, like components are indicated by the same numerals even where they are components of different assemblies and may not be repetitiously described for explanation.

DETAILED DESCRIPTION OF THE INVENTION

This invention relates to methods and apparatus for annuloplasty repair and replacement, characterized as using staples, or surgical clips (hereinafter referred to as "clips") of the so-called self-closing kind. A clip of a self-closing type may be broadly characterized as having two end points which tend to come closer together either by elasticity or so-called pseudoelasticity. Such a clip may be made by heat-treating a NiTi wire to a certain temperature and time to have a desired undeformed shape. Examples of such clips, including methods of making them as well as materials which may be used, were disclosed recently in aforementioned U.S. patent applications Ser. Nos. 09/089,884, 09/090,305, 09/259,705 and 09/260,623, comprising a wire of a shape memory alloy. For the purpose of the present invention, the minimum conditions such clips should satisfy include that they each have two end points, have a naturally closed configuration, can be forced to assume an open configuration but will tend to return to the naturally closed configuration by reducing the separation between these two end points if forced to assume the open configuration. The clips disclosed in aforementioned U.S. patent applications Ser. Nos. 09/089,884, 09/090,305, 09/259,705 and 09/260,623 (all herein incorporated by reference), comprising a deformable wire made of a shape memory alloy and assuming a U-shape when in the open configuration, satisfy all these required conditions.

Such a clip may be deployed, for example, in the form of a single-arm clip assembly as generally shown in FIG. 1 at 1, as well as in aforementioned U.S. patent applications Ser. Nos. 09/089,884 and 09/090,305, with a tissue-piercing needle 3 connected through a flexible member 4 such as a suture to one of the end points of such a clip 5 which is constrained to assume a generally U-shaped open configuration, the other end point of the clip 5 being formed as a stopper 6 for anchoring the clip 5 to the tissue, as will be explained below. A release mechanism 7, such as disclosed in aforementioned U.S. patent application Ser. No. 09/260,623, is provided such that the clip 5 can be easily released, say, by pressing thereon by a surgical instrument.

FIG. 2 illustrates a method of annuloplasty embodying this invention by using the single-arm clip assembly 1 of FIG. 1. The surgeon will guide the needle 3 to the surgical site, cause it to penetrate and pass through the tissue of the annulus sequentially at two positions one after the other which are circumferentially separated with respect to the annulus, and pull the flexible member 4 such that the clip 5 will have its two end points penetrate the tissue at these two positions. The stopper 6 serves to secure the clip 5 at this position. After the release mechanism 7 is pressed and the needle 3 is released from the clip 5, the clip 5 tends to return to its naturally closed configuration, tending to bring the two end points closer towards each other, thereby pinching the portion of the tissue therebetween. After one clip 5 is thus placed in the annulus, the same procedure is repeated with a plurality of other clips 5. These clips 5 are placed circumferentially, either serially or overlappingly, as shown in FIG. 2. Since the placed clips 5 tend to return to their naturally closed configurations by reducing the gap between their end points, the net effect is to reduce the circumference of the annulus.

FIGS. 3 and 4 show a clip delivery device 10 embodying this invention for carrying out an annuloplasty procedure in an alternative way. Broadly explained, the device 10 is comprised of an outer tube 20 with a hollow cylindrical interior and an elongated slit 25 at the bottom, affixed to a cap 22, a pusher 30 provided with a knob 32 and adapted to be pushed longitudinally inside the outer tube 20 for pushing one clip at a time, and a pair of cartridges 40 for mounting clips 50 thereon.

Each cartridge 40 is generally of a cylindrical shape attached to a fixture 41, as shown in FIGS. 5 and 6, with a quasi-circular cross-sectional shape and serves to have a plurality of clips 50 mounted thereon one next to another in a generally U-shaped open configuration with their end points pointing uniformly downward. The two cartridges 40 are positioned coaxially in a face-to-face relationship, extending perpendicularly to the slit 25 at the bottom of the outer tube 20, leaving therebetween a narrow gap 45 barely wide enough for one of the clips 50 to pass through vertically. Each carriage 40 is provided with a spring 42 such that the clips 50 mounted thereon are biased towards the gap 45. Each cartridge 40 has chamfered edge portion 47 adjacent the gap 45.

To assemble the device 10, the cartridges 40, fully loaded with the clips 50, are positioned inside the outer tube 20, as shown in FIGS. 3 and 4. The pusher 30 is inserted thereafter into the outer tube 20, and a spring 35 and the cap 22 are assembled onto the outer tube 20. Finally, the knob 32 is screwed into the pusher 30 to complete the clip delivery device 10.

In an annuloplasty procedure, the device 10, fully loaded with clips 50, is guided to a desired surgical site and oriented appropriately. As the knob 32 is pressed against the biasing force of the spring 35, the pusher 30 moves down and pushes one of the clips 50 which may originally have been on either of the cartridges 40 but has been pushed by the springs 42 to the position of the gap 45. Since the gap 45 is exactly above the slit 25 at the bottom of the outer tube 20, the clip 50 at the gap 45 is pushed out through the slit 25 to be inserted into the patient's tissue, both end points penetrating the tissue simultaneously at two positions that are separated circumferentially with respect to the annulus, as shown in FIG. 2, in the same way in which a staple is pushed out of a stapler of an ordinary kind.

Once thus deployed, the clip 50 tends to return to its naturally closed configuration, by reducing the distance between its two end points. Since the tissue is less firm than the cartridges 40, the portion of the tissue between the two end points of the clip 50 plicates to a certain extent, allowing the two end points of the clip 50 to come somewhat closer than when the clip 50 was kept on the cartridge 40. After a plurality of such clips 50 are thus implanted circumferentially as shown in FIG. 2, the net effect is to reduce the circumference of the annulus.

In the description of the device 10 above, the gap 45 was described as being barely wide enough to one of the clips 50 to be pushed down at a time, but this is not intended to limit the scope of the invention. There may be circumstances under which it is preferable to deploy a plurality of clips 50 at once. For situations like this, the gap 45 may be accordingly increased. In practice, it may be found advantageous to be provided with more than one such devices 10 each having a gap 45 of a different width such that different specified numbers of clips can be deployed from the provided devices 10.

Clip assemblies as shown at 1 in FIG. 1 may be used in a ring annuloplasty as shown, for example, in FIGS. 7A and 7B by using an annuloplasty ring 60 of a known kind. Although an open ring 60 is shown for illustration, a ring of a closed shape may be used. FIG. 7A shows the clip assembly 1 being used, with the needle 3 operated to penetrate the ring 60 at one position 60a, then into the tissue at one position 90a and out therefrom at another position 90b of the annulus and then again through the ring 60 at another position 60b. These positions 60a, 90a, 90b and 60b are selected such that the distance between the two positions 60a and 60b of penetration through the ring 60 is smaller than the distance between the position 90a of entry into the tissue by the needle 3 and the position 90b at which the needle 3 is pulled out of the tissue. After the stitching operation in an ordinary manner by the needle 3 described above is completed and the situation depicted in FIG. 7A is reached, the flexible member 4 is pulled until the clip 5 passes partially through the ring 60, its end point connected to the flexible member 4 having completely passed through the ring 60 twice and the other end point being stopped by the stopper 6 before penetrating the ring 60. This has the effect of contracting the portion of the tissue between the two positions 90a and 90b to the smaller distance between the two points of penetration 60a and 60b through the ring 60 by the needle 3 than the original separation of these two positions 90a and 90b of the tissue before the stitching is carried out. The flexible member 4 is thereafter released from the clip 5 by pressing the release mechanism 7, as described above. The clip 5, deployed while it was in an open configuration, has now only the ring 60 and the portion of the tissue between its two end points to prevent it from completely returning to its naturally closed configuration but still tends to reduce the distance separating the two end points. This internal force of the clip 5 tends to keep the ring 60 firmly attached to the tissue, thereby allowing the ring 60 to perform its intended function of keeping the annulus in its intended size.

FIG. 7B shows the ring 60 fastened around the annulus after a plurality of clips 5 have thus been deployed to keep the ring 60 at the surgical site. The clips 5 may be positioned to be circumferentially overlapping or separated. The two modes of arrangement may also be mixed.

The clip assembly 1 shown in FIG. 1 may be used also in a valve replacement procedure wherein mitral valve portions are removed and a mitral prosthesis sewing cuff is inserted.

The method of valve replacement according to this invention is again characterized as using clips of a self-closing kind as described above. FIG. 8A shows the clip assembly 1 being used, with the needle 3 operated to penetrate a mitral prosthesis sewing cuff 70 at one position, then into the tissue at one position where the prosthesis sewing cuff 70 is to be placed and out therefrom at another position of the tissue and then again through the prosthesis sewing cuff 70. After the situation depicted in FIG. 8A is reached, the flexible member 4 is pulled until the clip 5 passes partially through the prosthesis sewing cuff 70, its end point connected to the flexible member 4 completely passing through the prosthesis sewing cuff 70 twice and the other end point being stopped before penetrating the prosthesis sewing cuff 70 by the stopper 6. The flexible member 4 is thereafter released from the clip 5 by pressing the release mechanism 7, as described above. The clip 5, deployed while it was in an open configuration, has now only the prosthesis sewing cuff 70 and the portion of the tissue between its two end points to prevent it from returning to its naturally closed configuration but still tends to reduce the distance separating the two end points. This force of the clip 5 tends to keep the prosthesis sewing cuff 70 attached to the tissue.

Although the invention was described above with reference to only a limited number of embodiments, they are not intended to limit the scope of the invention. Many modifications and variations are possible within the scope of the invention. For example, a clip of the kind described above may be deployed in the form of a double-arm clip assembly as generally shown in FIG. 9 at 101, as well as in aforementioned U.S. patent applications Ser. Nos. 09/259,705 and 09/260,623, having a tissue-piercing needle 3 connected through a flexible member 4 such as a suture to each of the end points of a clip 5, maintained in its generally U-shaped open configuration. A release mechanism 7 is provided at each end point of the clip 5 such that the clip 5 can be easily released from the flexible member 4.

FIG. 10 shows the double-arm clip assembly 101 being used in a ring annuloplasty process. The pair of needles 3 are each caused to penetrate the tissue and be pulled out and then penetrate through a ring 60 such that the distance between the two positions at which the needles 3 are caused to penetrate and come out of the tissue is greater than the distance between the two positions on the ring 60 where the needles 3 pass through the ring 60, as explained above with reference to FIG. 7A. After the stitching with the needles 3 as described above is completed and the situation depicted in FIG. 10 is reached, the flexible member 4 is pulled until the both end points of the clip 5 in its open configuration pass through the tissue and the ring 60. The flexible members 4 are then released from the clip 5 by pressing the release mechanisms 7, and the tendency of the clip 5 to coil up and return to its closed configuration serves to keep the ring 60 firmly attached to the tissue, as explained above with reference to the single-arm clip assembly 1.

What is claimed is:

1. A mitral valve repair method comprising the steps of:

providing clips each having two end points which are separated from each other when in an open configuration and tending to return to a naturally closed configuration by reducing distance between said end points when in said open configuration;

placing an annuloplasty ring about an annulus; and attaching said ring around said annulus by causing said clips to pass through said ring, wherein each of said clips has a tissue-penetrating needle releasably attached through a flexible member to one of said two end points thereof and said step of attaching said ring comprises the steps of:

causing the needle associated with said each clip to penetrate and pass through said ring and tissue of said annulus; and thereafter pulling said flexible member to position said each clip so as to hold said ring to said tissue, wherein said needle is caused to pass through said ring at two positions separated by a shorter distance, to penetrate said tissue at one position and to come out therefrom at another position separated from said one position by a larger distance than said shorter distance.

2. The repair method of claim 1 wherein said clips are attached to said ring in circumferential directions along said ring.

3. The repair method of claim 1 wherein said clips are each generally U-shaped when in said open configuration, comprising a wire of a shaped memory material.

\* \* \* \* \*